US00PP36006P2

(12) United States Plant Patent
Kordes

(10) Patent No.: US PP36,006 P2
(45) Date of Patent: Jul. 16, 2024

(54) MINIATURE ROSE PLANT NAMED 'KORpot127'

(50) Latin Name: *Rosa hybrida*
Varietal Denomination: KORpot127

(71) Applicant: W. KORDES' SÖHNE ROSENSCHULEN GMBH & CO KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/396,793

(22) Filed: Dec. 27, 2023

Related U.S. Application Data

(60) Provisional application No. 63/442,210, filed on Jan. 31, 2023.

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121
CPC ..... A01H 6/749; A01H 5/02
See application file for complete search history.

(56) References Cited

U.S. PATENT DOCUMENTS

| | | | |
|---|---|---|---|
| PP22,811 | P2 | 6/2012 | Kordes |
| PP23,604 | P3 | 5/2013 | Olesen |
| PP29,042 | P3 | 3/2018 | Kordes |

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot127', is described. The new variety 'KORpot127' forms in abundance on a substantially continuous basis attractive, light lavender-colored blossoms. The vegetation is vigorous and the growth habit is compact. Attractive dark green, semi-glossy foliage is formed.

1 Drawing Sheet

Latin name of genus and species of plant claimed: *Rosa hybrida.*

Variety denomination: 'KORpot127'.

STATEMENT REGARDING PRIOR DISCLOSURES BY THE INVENTOR

The first offer for sale of the new variety was February 2022, in the U.S.A. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding in 2016 at Offenseth-Sparrishoop, Germany by artificial pollination wherein two parents were crossed which previously had been studied in the hope that they would contribute the desired characteristics. The female parent (i.e., the seed parent) of the new variety was the 'KORpot022' (U.S. Plant Pat. No. 22,811). The male parent (i.e., the pollen parent) of the new variety was the 'Poulpar058' variety (U.S. Plant Pat. No. 23,604).

The parentage of the new variety can be summarized as follows:

'KORpot022' x 'Poulpar058'

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms attractive, light lavender-colored blossoms,
(b) exhibits a compact growth habit,
(c) forms vigorous vegetation, and
(d) forms attractive ornamental semi-glossy foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the 'KORpot022' variety (i.e., the seed parent) displays a lower petal count and lower number of blooms in clusters compared to the new variety. Additionally, the 'POULpar058' variety (i.e., the pollen parent) provides a less compact growth habit compared to the new variety and displays mauve-colored flowers, whereas the new variety displays light lavender-colored flowers. Moreover, the new variety can be readily distinguished from non-parental related similar varieties. For example, 'KORpot064' (U.S. Plant Pat. No. 29,042) displays a pink flower color whereas the new variety displays a light lavender flower color.

The new variety has been named the 'KORpot127' variety.

BRIEF DESCRIPTION OF THE PHOTOGRAPHS

The accompanying photograph shows, as nearly true as it is reasonably possible to make the same in a color illustration of this character, typical specimens of the new variety and blossoms of the new variety. The illustrated rose plants of the new variety were approximately sixteen weeks of age and were grown indoors in 4-inch containers on their own roots at Surrey, British Columbia, Canada.

Drawing—illustrates specimens of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a one-year-old specimen of the new variety, observed during September, while growing on its own roots in a greenhouse in a one-gallon container in Cochranville, Pennsylvania.

Botanical classification: *Rosa hybrida* cultivar 'KORpot127'.

Commercial classification: Miniature Rose.

Plant:

*Height.*—Approximately up to 39.0 cm.

*Width.*—Approximately up to 33.0 cm.

*Habit.*—Compact.

Branches:

*Stem color.*—Commonly Green Group 143A.

*Length.*—Main stems: approximately 39.0 cm on average. — secondary stems: approximately 18.0 cm on average.

*Diameter.*—Main stems: approximately 8.0 mm on average. — secondary stems: approximately 3.0 mm on average.

*Texture.*—Glabrous.

*Thorns.*—Amount: moderate. — young thorns: length is approximately 4.0 mm on average; width is approximately 1.0 mm at point of attachment; and color is commonly Orange Group 26C.

Leaflets:

*Number.*—3, 5, and 7.

*Shape.*—Ovate; apex is acute; and base is rounded.

*Arrangement.*—Odd-pinnate.

*Venation pattern.*—Reticulate.

*Margin.*—Serrate.

*Glossiness of upper side.*—Semi-glossy.

*Texture.*—Upper surface: smooth. — under surface: smooth.

*Size.*—Terminal leaflet: length is approximately 3.0 cm on average; width is approximately 2.0 cm on average. — lower leaflets: length is approximately 2.3 cm on average; width is approximately 1.5 cm on average. — 5-Leaflet leaf: length is approximately 7.0 cm on average; width is approximately 4.0 cm on average.

Foliage:

*Young foliage.*—Upper surface color: commonly Green Group 137C with indistinguishable venation. — under surface color: commonly a blend of Yellow-Green Group 148A and Greyed-Orange Group 176C with venation commonly Yellow-Green Group 146C.

*Old foliage.*—Upper surface color: commonly Green Group 137A with indistinguishable venation. — under surface color: commonly Green Group 138A with venation commonly Green Group 139C.

*Petiole.*—Length: approximately 2.0 cm on average. — diameter: approximately 2.0 mm on average. — texture: upper surface is smooth; under surface is mostly smooth with sparse prickles. — upper surface color: commonly Green Group 143A. — under surface color: commonly Green Group 143B.

*Rachis.*—Length: approximately 1.7 cm on average. — diameter: approximately 1.0 mm on average. — upper surface color: commonly Green Group 143A. — under surface color: commonly Green Group 143B.

*Stipules.*—Length: approximately 7.0 mm on average. — width: approximately 2.0 mm on average. — margin: entire to erose. — upper surface color: commonly Green Group 143A. — lower surface color: commonly Green Group 143B.

Inflorescence:

*Number of flowers.*—About 9 blooms on average on a plant at once.

*Number of blossoms per stem or in a cluster.*—Typically 1 and 4 blooms per stem on average.

*Peduncle.*—Color: commonly Green Group 143A. — diameter: approximately 3.0 mm on average. — length: approximately 4.0 cm on average. — surface texture: glabrous. — strength: strong.

*Sepals.*—Number: 5. — upper surface color and texture: commonly Green Group 143B, covered in short pubescence. — under surface color and texture: commonly Green Group 143C, puberulent. — size: length is approximately 1.5 cm on average; width is approximately 1.0 cm on average. — margin: entire with extension on two or three sepals measuring 7.0 mm in length and 2.0 mm in width. — undulation of leaf margin: moderate, medium. — shape: lanceolate. — apex: acute to aristate. — base: truncate or flat as it joins the receptacle.

*Buds.*—Shape: globular. — size: length is approximately 1.5 cm on average; width is approximately 1.5 cm on average. — color (when opening): commonly Purple Group 75A.

*Flower.*—Form: double, cuplike. — profile: flat. — diameter: approximately 4.0 cm on average. — height: approximately 2.0 cm on average. — duration: on the plant approximately 20 days. — petal color when first and fully opened: upper surface is commonly Purple Group 75B with a basal spot of White Group 155B; under surface is commonly Purple Group 75C with basal spot of White Group 155B. — petal color when fading: upper and under surfaces are commonly Purple Group 75D with hint of Red-Purple Group 69C.

*Fragrance.*—Very light, sweet.

*Petal.*—Number: 60 on average. — drop: average for the type. — reflex one by one: yes. — texture of upper and lower surfaces: glabrous. — length: inner petals are approximately 1.0 cm on average and outer petals are approximately 2.0 cm on average. — width: inner petals are approximately 5.0 mm on average and outer petals are approximately 2.0 cm on average. — overall shape: broadly obovate. — margin: entire. — margin undulation: medium. — apex shape: rounded to cuspidate. — base shape: rounded to cuneate.

*Petaloids.*—Number: commonly 5 per flower. — color upper and under surfaces: commonly Purple Group 75C with a basal spot of Yellow Group 4D. — length: approximately 5.0 mm on average. — width: approximately 3.0 mm on average. — texture: smooth. — margins: variable, entire to erose. — shape: rounded and mostly curving inward. — apex: round. — base: cuneate.

*Stamen.*—Number: approximately 50. — anthers: number is approximately 50; color is commonly Yellow Group 11C; length is approximately 1.5 mm on average; and shape is oval. — filaments: length is approximately 1.5 mm on average and color is commonly Green-Yellow Group 1B.

*Pistils.*—Arrangement: separate and free. — number: approximately 70. — style: length is approximately 5.0 mm and color is commonly Green-Yellow Group 1B at the base, transitioning to Purple Group 75A at the apex. — stigma: diameter is commonly less than 1.0 mm; shape is fan shaped; and color is commonly Green-Yellow Group 1B.

*Receptacle.*—Diameter: approximately 8.0 mm on average. — shape: urn shaped. — color: commonly Green Group 143A. — surface texture: smooth.

*Pollen.*—None observed.

*Hips/seed.*—None observed.

Development:

*Vegetation.*—Dark green, vigorous, and strong.

*Blossoming.*—Abundant and substantially continuous; blooms may continue year-round if grown inside a warm greenhouse.

*Resistance to diseases.*—Good resistance for powdery mildew (*Sphaerotheca pannosa*) disease under normal greenhouse growing conditions in Cochranville, Pennsylvania.

*Hardiness.*—Unknown.

The new 'KORpot127' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot127' characterized by the following combination of characteristics:

(a) forms attractive, light lavender-colored blossoms, (b) exhibits a compact growth habit, (c) forms vigorous vegetation, and (d) forms attractive ornamental semi-glossy foliage;

substantially as herein shown and described.

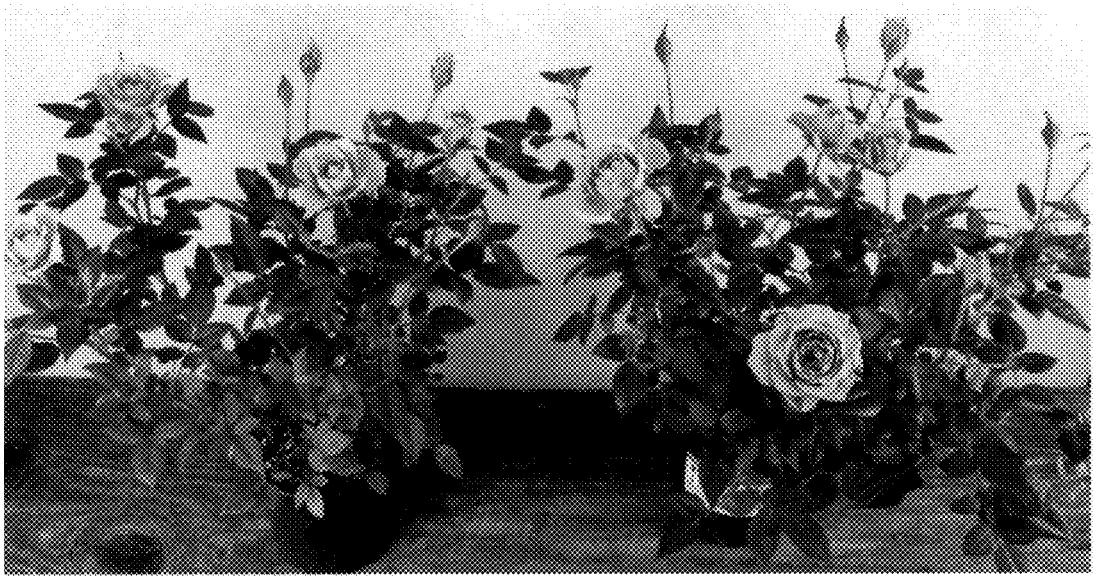

* * * * *